United States Patent
Yu et al.

(10) Patent No.: US 11,773,454 B2
(45) Date of Patent: Oct. 3, 2023

(54) MULTIPLEX PCR AMPLIFICATION METHOD FOR SPECIES AND HUMAN INDIVIDUAL RECOGNITION AND IDENTIFICATION OF UNKNOWN BIOLOGICAL SAMPLE SUSPECTED TO BE FROM HUMAN

(71) Applicant: NINGBO HEALTH GENE TECHNOLOGIES CO., LTD., Zhejiang (CN)

(72) Inventors: Ding Yu, Zhejiang (CN); Yong Wu, Zhejiang (CN); Haiying Jin, Zhejiang (CN); Kang Wang, Zhejiang (CN)

(73) Assignee: NINGBO HEALTH GENE TECHNOLOGIES CO., LTD., Zhejiang (CN)

( * ) Notice: Subject to any disclaimer, the term of this patent is extended or adjusted under 35 U.S.C. 154(b) by 124 days.

(21) Appl. No.: 16/971,706

(22) PCT Filed: Jan. 16, 2019

(86) PCT No.: PCT/CN2019/071888
§ 371 (c)(1),
(2) Date: Aug. 21, 2020

(87) PCT Pub. No.: WO2019/165858
PCT Pub. Date: Sep. 6, 2019

(65) Prior Publication Data
US 2021/0025013 A1    Jan. 28, 2021

(30) Foreign Application Priority Data
Feb. 27, 2018   (CN) .......................... 201810164089.3

(51) Int. Cl.
*C12Q 1/6888* (2018.01)

(52) U.S. Cl.
CPC ..... *C12Q 1/6888* (2013.01); *C12Q 2600/156* (2013.01); *C12Q 2600/16* (2013.01)

(58) Field of Classification Search
CPC combination set(s) only.
See application file for complete search history.

(56) References Cited

FOREIGN PATENT DOCUMENTS

| | | |
|---|---|---|
| AT | 508890 A1 | 4/2011 |
| CN | 101838689 A | 9/2010 |
| CN | 102286476 A | 12/2011 |
| CN | 103320511 A | 9/2013 |
| CN | 104131072 A | 11/2014 |
| CN | 104946632 A | 9/2015 |
| CN | 105177125 A | 12/2015 |
| CN | 106755414 A | 5/2017 |
| CN | 106868150 A | 6/2017 |
| CN | 108384842 A | 8/2018 |
| WO | WO 03/031646 A1 | 4/2003 |
| WO | WO 2016/188144 | 2/2016 |
| WO | WO 2016/188331 | 12/2016 |
| WO | WO 2019/165858 | 9/2019 |

OTHER PUBLICATIONS

Kanthaswamy et al. (Forensic Science International: Genetics 6 (2012) 290-295).*
Solt et al. (NIJ grant No. 2008-DN-BX-K288, pp. 1-59).*
Koppel (Eur Food Res Technol 2009 230:125-133).*
Zhang et al. (Forensic Science International: Genetics 17 (2015) 61-69).*
Bataille (Forensic Science International, 1999, 99, pp. 165-170).*
Kullberg (Mol Biol Evol, 2006, 23(8):1493-150).*
International Search Report and Written Opinion dated Apr. 17, 2019 for Patent Application No. PCT/CN2019/071888, which was filed on Jan. 16, 2019 and published as WO 2019/165858 on Sep. 6, 2019 (Inventor—Yu et al.; Applicant—Ningbo Health Gene Technologies Co., Ltd.) (19 pages).
International Preliminary Report on Patentability dated Aug. 27, 2020 for Patent Application No. PCT/CN2019/071888, which was filed on Jan. 16, 2019 and published as WO 2019/165858 on Sep. 6, 2019 (Inventor—Yu et al.; Applicant—Ningbo Health Gene Technologies Co., Ltd.) (5 pages).
Bellis, C. et al., "A Molecular Genetic Approach for Forensic Animal Species Identification," Forensic Science International, vol. 134, pp. 99-108, Dec. 31, 2003.
Linacre, A. et al., "ISFG: Recommendations regarding the Use of Non-human (Animal) DNA in Forensic Genetic Investigations," Forensic Science International: Genetics, vol. 5, pp. 501-505, Dec. 31, 2011.
Janyaporn P., et al. "Genetic Profiling Reveals Cross-Contamination and Misidentification of 6 Adenoid Cystic Carcinoma Cell Lines: ACC2, ACC3, ACCM, ACCNs, ACCS, and CAC2", PLOS One, vol. 4, No. 6, Jun. 25, 2009, pp. e6040.
Raymond. W. N., et al., "Short Tandem Repeat Profiling: Part of an Overall Strategy for Reducing the Frequency of Cell Misidenfitication", In Vitro Cellular and Developmental Biology—Animal, vol. 46, No. 10, Oct. 7, 2010, pp. 811-819.
Suresh V. K., "18S rRNA is a Reliable Normalisation Gene for Real Time PCS based on Influenza Virus Infected Cells", Virology Journal, Biomed Central, vol. 9, No. 1, Oct. 8, 2012, pp. 230.

(Continued)

*Primary Examiner* — Sarae L Bausch
(74) *Attorney, Agent, or Firm* — BALLARD SPAHR LLP

(57) ABSTRACT

Provided is a multiplex PCR amplification method for identifying an unknown biological sample suspected to be from a human. The method comprises the following steps: 1) acquiring an unknown biological sample suspected to be from a human and which is to be detected; 2) directly adding said unknown sample or nucleic acid extracted from said unknown sample to a premixed PCR reagent; 3) running a PCR amplification program to conduct a multiplex PCR amplification reaction; and 4) detecting and analyzing PCR amplification products, wherein the premixed PCR reagent contains primers specific to human genetic markers and primers specific to nuclear chromosomal genes of non-human species. Also provided is a multiplex PCR amplification kit for species and human individual recognition and identification of an unknown biological sample.

7 Claims, 7 Drawing Sheets

Specification includes a Sequence Listing.

(56) References Cited

OTHER PUBLICATIONS

Pozo Talia Del et al. "Identification of reference genes for guantitative real-time PCR studies in human cell lines under copper and zinc exposure", Biometals, vol. 29, No. 5, Aug. 27, 2016, pp. 935-944.
Perez-Rico et al. "Determining ACTB, ATP5B and RPL32 as optimal reference genes for quatitative RT-PCR studies of cryopreserved stallion semen." Animal Reproduction Science, vol. 149, No. 3-4, Aug. 28, 2014, pp. 204-211.
Turabelidze Anna et al. "Importance of housekeeping gene selection for accurate reverse transcription-quantitative polymerase chain reaction in a wound healing model: Accurate RT-gPCR in a wound healing model" Wound Repair and Regeneration.
Office Action dated Mar. 29, 2023 by the European Patent Office for Application No. 1976195, filed Jan. 16, 2019 (10 pages).

\* cited by examiner

MULTIPLEX PCR AMPLIFICATION METHOD FOR SPECIES AND HUMAN INDIVIDUAL RECOGNITION AND IDENTIFICATION OF UNKNOWN BIOLOGICAL SAMPLE SUSPECTED TO BE FROM HUMAN

CROSS-REFERENCE TO RELATED APPLICATIONS

This application is a U.S. National Phase Application of International Application No. PCT/CN2019/07188, filed Jan. 16, 2019, which claims priority to Chinese Application No. 201810164089.3, filed Feb. 27, 2018, each of which are hereby incorporated by reference in their entirety.

REFERENCE TO SEQUENCE LISTING

The Sequence Listing submitted Oct. 16, 2020 as a text file named "16188_0016U1_Updated_Sequence_Listing," created on Oct. 16, 2020, and having a size of 9,317 bytes is hereby incorporated by reference pursuant to 37 C.F.R. § 1.52(e)(5).

FIELD OF THE INVENTION

The present invention relates to a multiplex PCR amplification method and the application thereof, in particular to a fluorescent multiplex amplification method for simultaneously detecting 21 chromosomal loci, 1 Y-chromosome STR, 1 gender locus, and 4 non-human species-specific DNA sequences in a single tube, and the application thereof, and belongs to the fields of chromosome typing and identification, and also of animal molecular biology.

BACKGROUND

Short tandem repeats (STRs) are a class of DNA sequences with length polymorphism that are usually formed from 2-6 bases as the core units repeated in tandem in the human genome. The varying number and repeat times of the core units constitutes the genetic polymorphism of STRs. A large amount of STRs are widely distributed throughout the human genome, accounting for approximately 10% of that genome, and thus are highly informative. Various sequences give rise to hundreds of millions of genotype combinations, and each of them occurs at very low frequency in the population and exhibits excellent capability to identify an individual. Moreover, the STR loci with small fragments are more prone to amplification and suitable for detecting trace amounts of tested materials that have been degraded. As each of STR loci can be amplified under similar conditions, they are appropriate for multiplex amplification, which has the advantages of being highly sensitive, accurate, rapid, and hugely informative. Therefore, the STR loci are often used as genetic markers in DNA analytic technology for forensic individual identification and paternity testing.

During the identification of an individual, the source of a sample is affected by the environment and has a very complicated make-up. Typically, a human sample may be contaminated by non-human species or even in some environments interfered apparently by non-human species (such as blood stains), resulting in a sample with lower content or even loss of human-derived DNA. If a sample is detected using only human STR assay kit, circumstances such as lower sample peak, interference with non-specific peak, or even absence of sample peak will be observed so that the person who handles the case cannot immediately determine whether there are too many inhibitors in the sample or whether the DNAs are degraded or present at lower concentrations. It is always required to conduct two or more tests, re-confirm the results on the scene, and determine the source of the sample through further investigation.

Suitable methods that can be employed for identifying non-human species as currently reported in the relevant documents mainly include: 1) the PCR method established by designing species-specific primers based on differences in the mitochondrial DNA (such as cytochrome b (Cytb) gene) sequences (see CN 102876805A); however, mitochondrial DNAs have high copy number, varying amounts in different tissues, and poor stability, and thus it is difficult to perform quantitative analysis on them; for example, the sequence of Cytb is highly similar among different species and thus is inappropriate for multiplex amplification; moreover, false positive results may arise when the concentration of a sample is high; and 2) Species STR-based detection methods (see CN104928387A); however, since STRs are sequences that are highly polymorphic in length, they may occupy a larger portion of the detection range; if combined with detection of human STRs, the multiplex detection quantity for non-human species would be very limited when the detection quantity for human STRs is guaranteed, resulting in lower space utility efficiency within the detection range; if STRs from different species are to be detected jointly in one assay, in practical application they cannot be detected and determined simultaneously by just one test, and multiple amplification and detection are also required. This might be helpful for discriminating purely non-human species to some extent; however, in the case where the human DNAs are contaminated by a non-human sample, the person who conducts the assay would be unable to immediately acquire accurate information about the sample. If there are non-specific amplification peaks for some species in the detection of STRs, the determination of results would be interfered or misinterpreted. Therefore, the assays carried out by such a method are highly restricted and are of little assistance for economizing the resources and improving efficiency.

In summary, no relevant research or report on a method of detecting human DNA genetic markers for individual identification while simultaneously identifying non-human species has been available yet. To fulfill this need, the present invention provides a detection scheme that is capable of identifying a human-derived sample comprising components of non-human species in a rapid, convenient and accurate manner with high-sensitivity and high-specificity.

SUMMARY OF THE INVENTION

The present invention provides a method for rapidly identifying an unknown biological sample suspected to be from human by conducting a joint specific detection of preferable human DNA genetic markers and DNA sequences of housekeeping genes on chromosomes of preferable target non-human species, which can determine in a single assay whether the unknown biological sample is a human-derived sample or a human-derived sample blended with components of other species; if the sample is (or does contain) a human-derived sample, it will be individually identified synchronously. In particular, the present invention provides a multiplex PCR amplification method for species and human individual identification on an unknown biological sample suspected to be from human, which comprises the steps of:
1) collecting an unknown biological sample to be detected, which is suspected to be from human;
2) adding the unknown biological sample to be detected directly, or nucleic acids extracted from the unknown biological sample to be detected, into premixed PCR reagents;
3) performing multiplex PCR amplification by running PCR amplification procedures;
4) detecting and analyzing the PCR amplification products;

wherein the premixed PCR reagents comprise primers specific for human DNA genetic markers and primers specific for nuclear genes on the chromosomes of non-human species.

The method for detecting and analyzing PCR amplification products comprises identifying differences in the sizes of PCR product fragments and conducting sequencing analysis on the sequences of PCR products; preferably, the PCR products in the present invention are detected and analyzed by identifying differences in the sizes of the PCR product fragments. Suitable identification methods include polyacrylamide gel electrophoresis, agarose gel electrophoresis and capillary gel electrophoresis. In particular, capillary gel electrophoresis is used in the present invention, which can be divided into single-wavelength and multiple-wavelength methods according to the wavelengths to be detected; preferably, the detection method used herein is a method with 6 optical wavelengths.

According to the present invention, the method for individual identification on a human-derived sample is performed by detecting human DNA genetic markers, including InDel sites, SNP sites and STR loci; preferably, 22 human STR loci, including D3S1358, TH01, D21S11, D18S51, Penta E, D12S391, D6S1043, D2S1338, D1S1656, D5S818, D13S317, D7S820, D19S433, CSF1PO, Penta D, vWA, D8S1179, TPOX, FGA, D2S441, D16S539 and DYS391, as well as a gender recognition site Amel (non-STR locus), are used herein.

The non-human species of the present invention include non-human mammals, such as non-human primates, cats, dogs, sheep, goats, horses, cow, pigs, and rodents; and non-mammals, such as birds, domestic poultry, reptiles, amphibians; preferably, the non-human species used herein are chickens, ducks, geese and pigs.

In the present invention, non-human species are identified by aligning the nucleotide sequences of the same genes among different species and designing species-specific primers and/or probes at locations where the sequences are different to achieve rapid detection and identification of the species. The genes useful for the identification of non-human species may be all the genes that are present on chromosomes of all the species to be identified but are somewhat different in their sequences, such as housekeeping genes in the genome on chromosomes, including genes encoding tubulin, ATP synthase, glycolytic enzymes, ribosomal proteins, etc. Preferably, the housekeeping gene used herein is ATP5B gene.

Nuclear genes on chromosomes that are suitable for use in the present invention can ensure that the copy number of nucleic acids in the detected sample is independent of different tissue sources, different life cycles or the like. Preferred housekeeping gene sequences are relatively conservative and stable in genetic evolution, and have significant difference among different species while little difference in the same category of species; they have high species-specificity.

The present invention further provides a multiplex PCR amplification kit for rapidly identifying an unknown biological sample to be detected that is suspected to be from human to determine whether the sample is a human-derived sample or a human-derived sample blended with (or containing) other components of non-human species; if the sample is (or does contain) a human-derived sample, it will be individually identified synchronously. In particular, the kit of the present invention is characterized in comprising primers specific for human DNA genetic markers and primers specific for nuclear genes on the chromosomes of non-human species, which can be used for synchronous multiple amplification of the following human DNA genetic markers and housekeeping genes on the chromosomes of non-human species: D3S1358, TH01, D21S11, D18S51, Penta E, D12S391, D6S1043, D2S1338, D1S1656, D5S818, D13S317, D7S820, D19S433, CSF1PO, Penta D, vWA, D8S1179, TPOX, FGA, D2S441, D16S539, DYS391, and Amel as well as chicken ATP5B, duck ATP5B, goose ATP5B and pig ATP5B.

By performing synchronous PCR amplification of human DNA genetic markers and housekeeping genes from non-human species, the method of the present invention can fulfill joint detection in a single tube for a plurality of species, and further realize synchronous identification of multiple non-human species and various individual identification sites for a human-derived sample. The present method has the advantages of accuracy, high sensitivity, convenience and high specificity, and avoids using multiple PCRs in the current amplification method for identifying origins of species, and thus further avoids wasting resources such as tested samples and testing reagents. When multiple amplifications are not possible due to a small amount of samples, the present method can still succeed in accomplishing the identification.

DETAILED DESCRIPTION OF THE INVENTION

Figure 1:
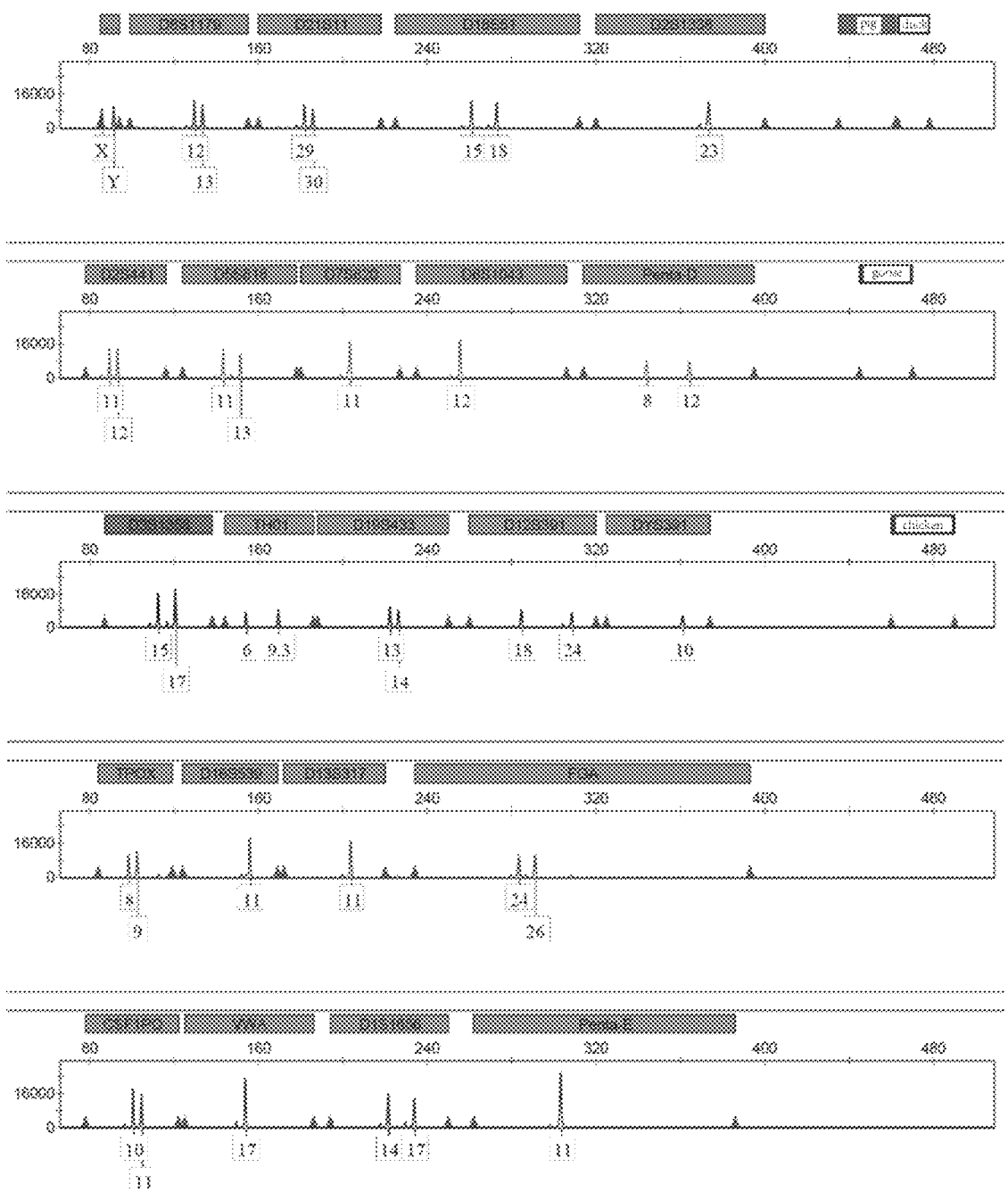
FIG. 1 illustrates a diagram of Control DNA 9948 sample.
Figure 2:
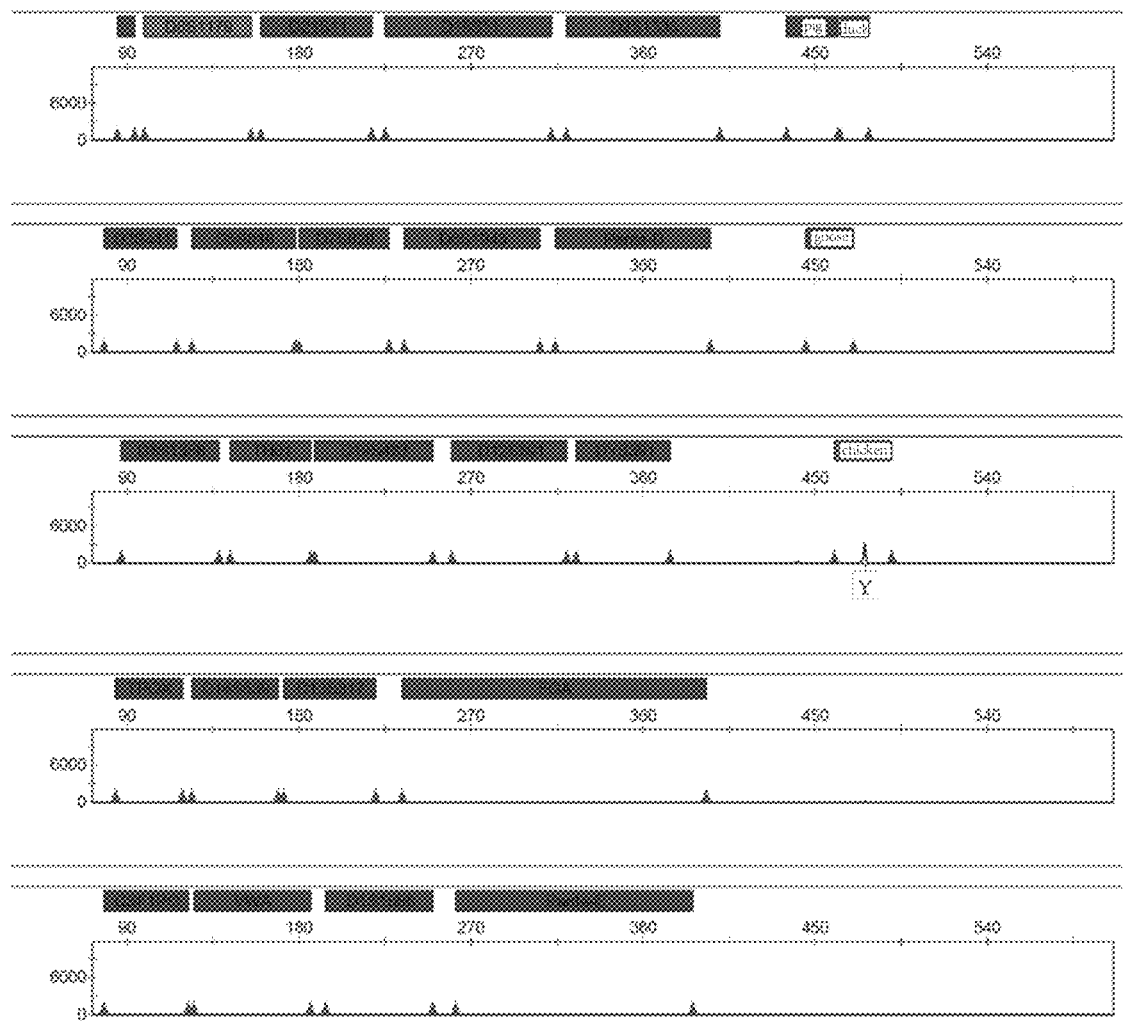
FIG. 2 illustrates a diagram of DNA samples extracted from chickens after amplification.
Figure 3:
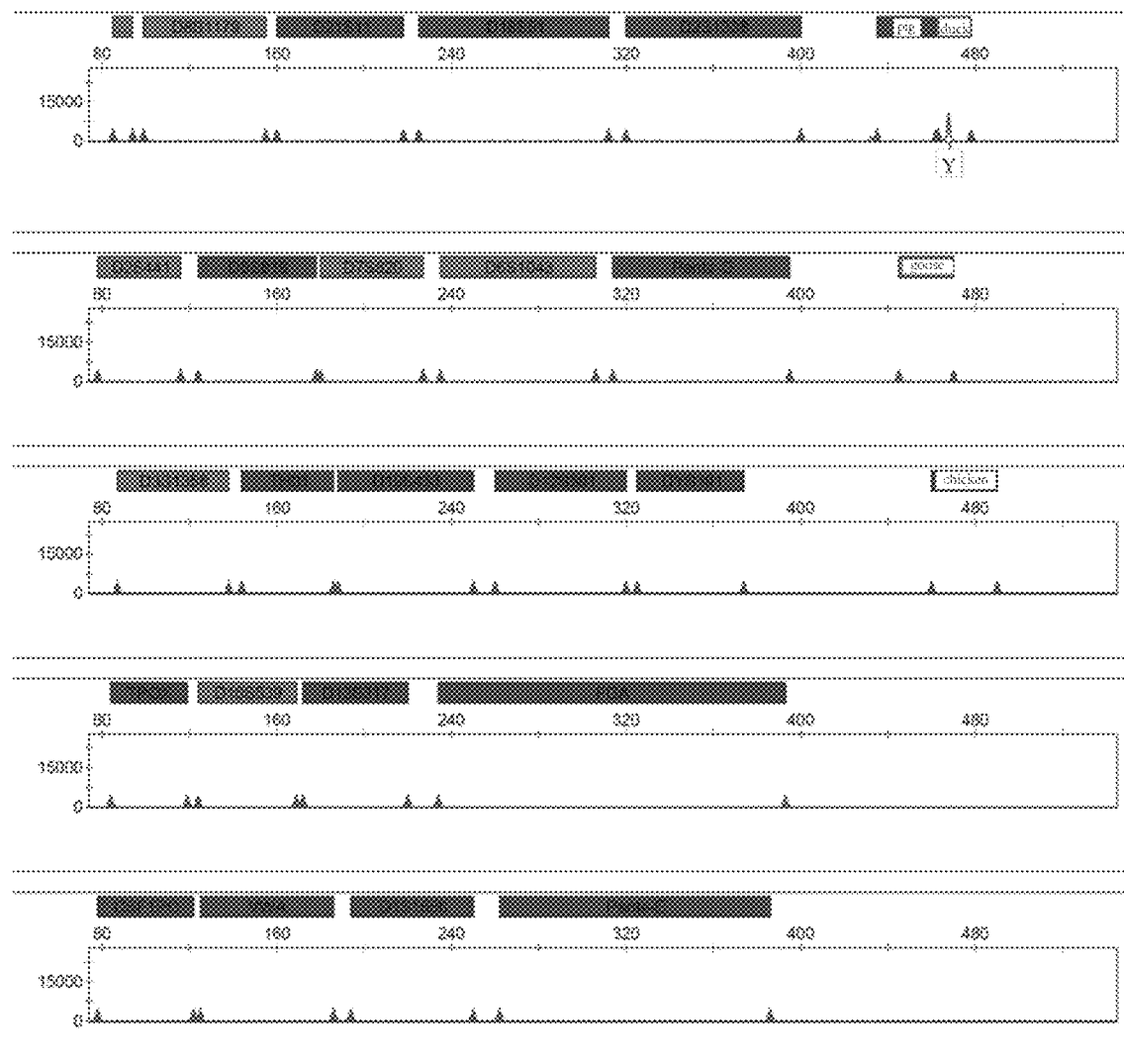
FIG. 3 illustrates a diagram of DNA samples extracted from ducks after amplification.
Figure 4:
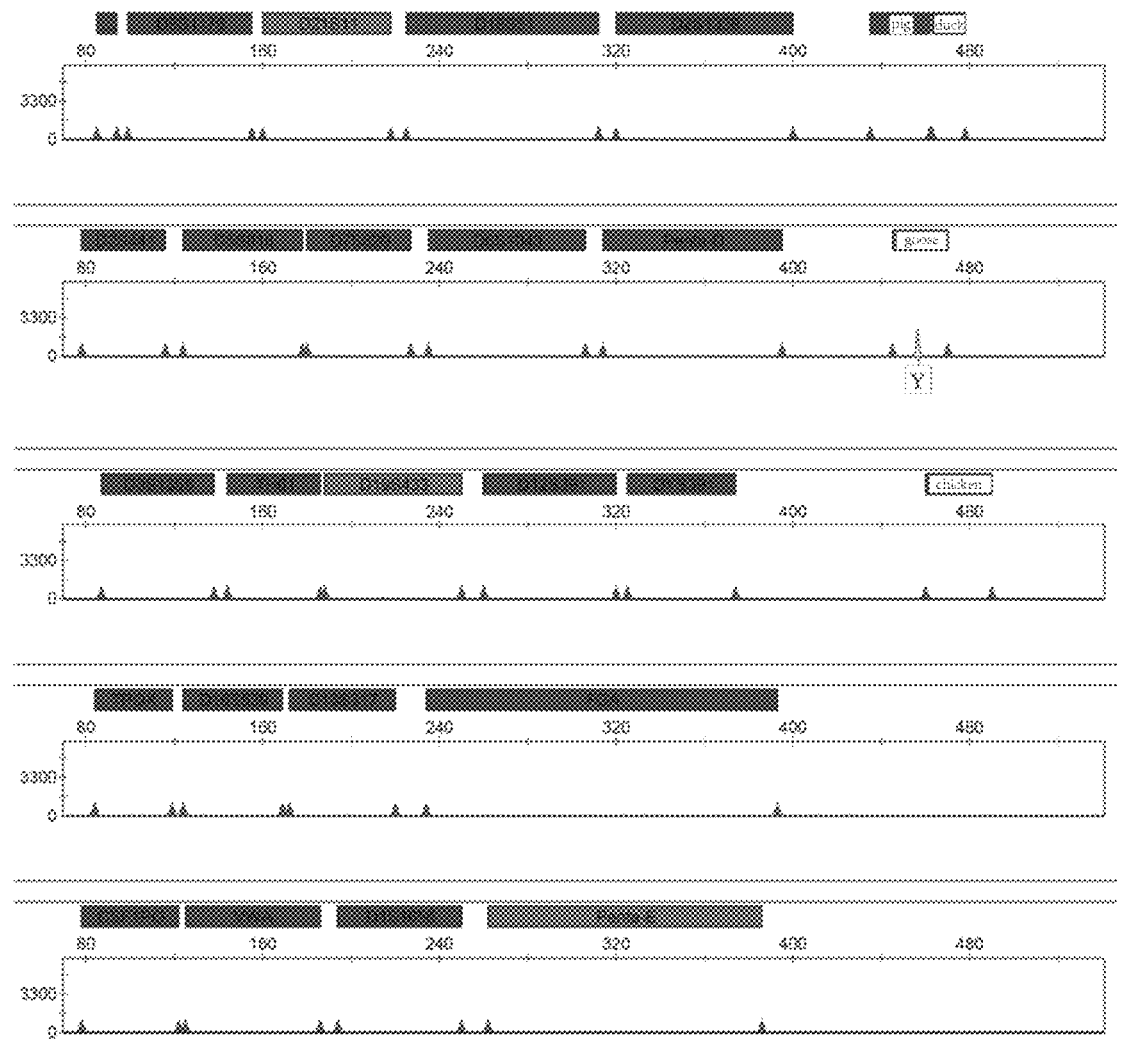
FIG. 4 illustrates a diagram of DNA samples extracted from geese after amplification.
Figure 5:
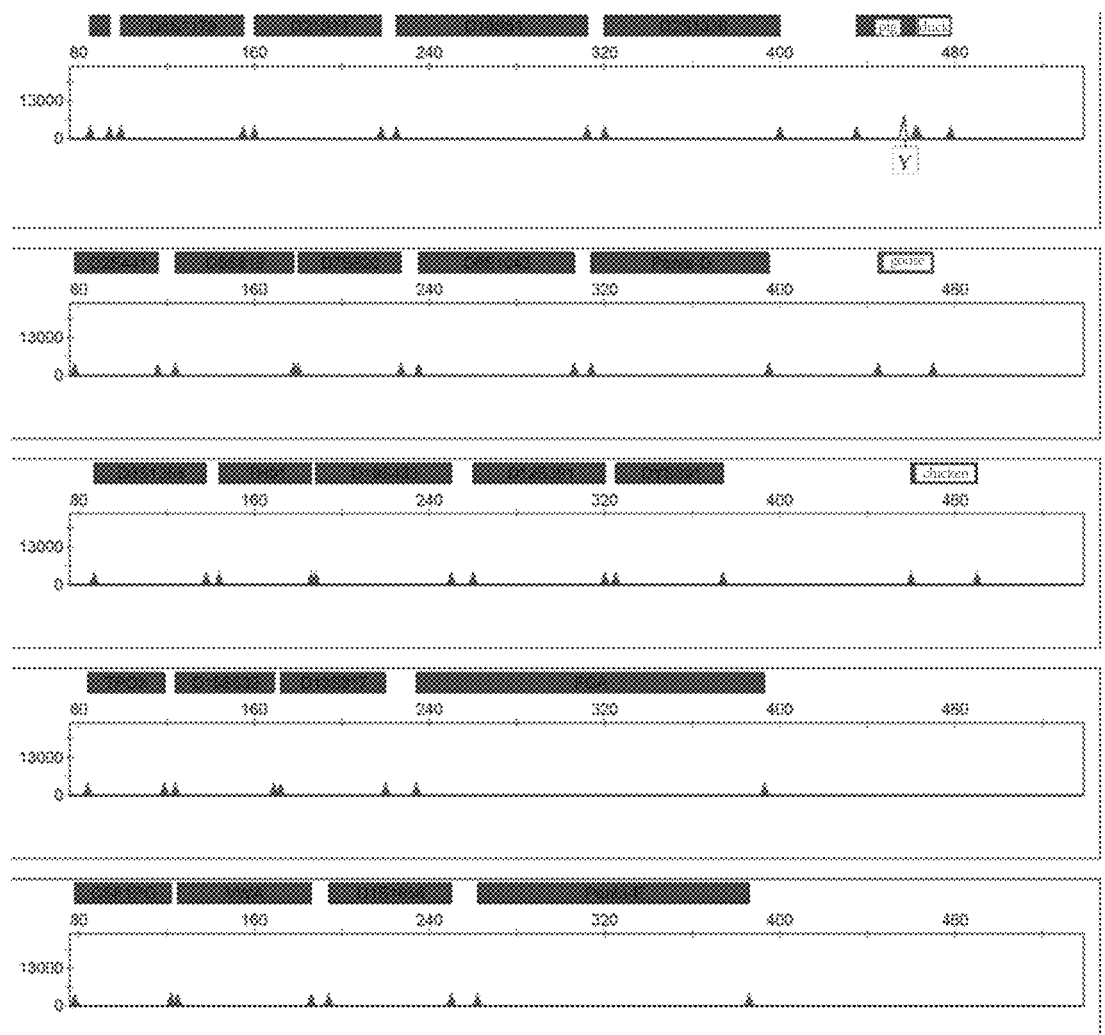
FIG. 5 illustrates a diagram of DNA samples extracted from pigs after amplification.
Figure 6:
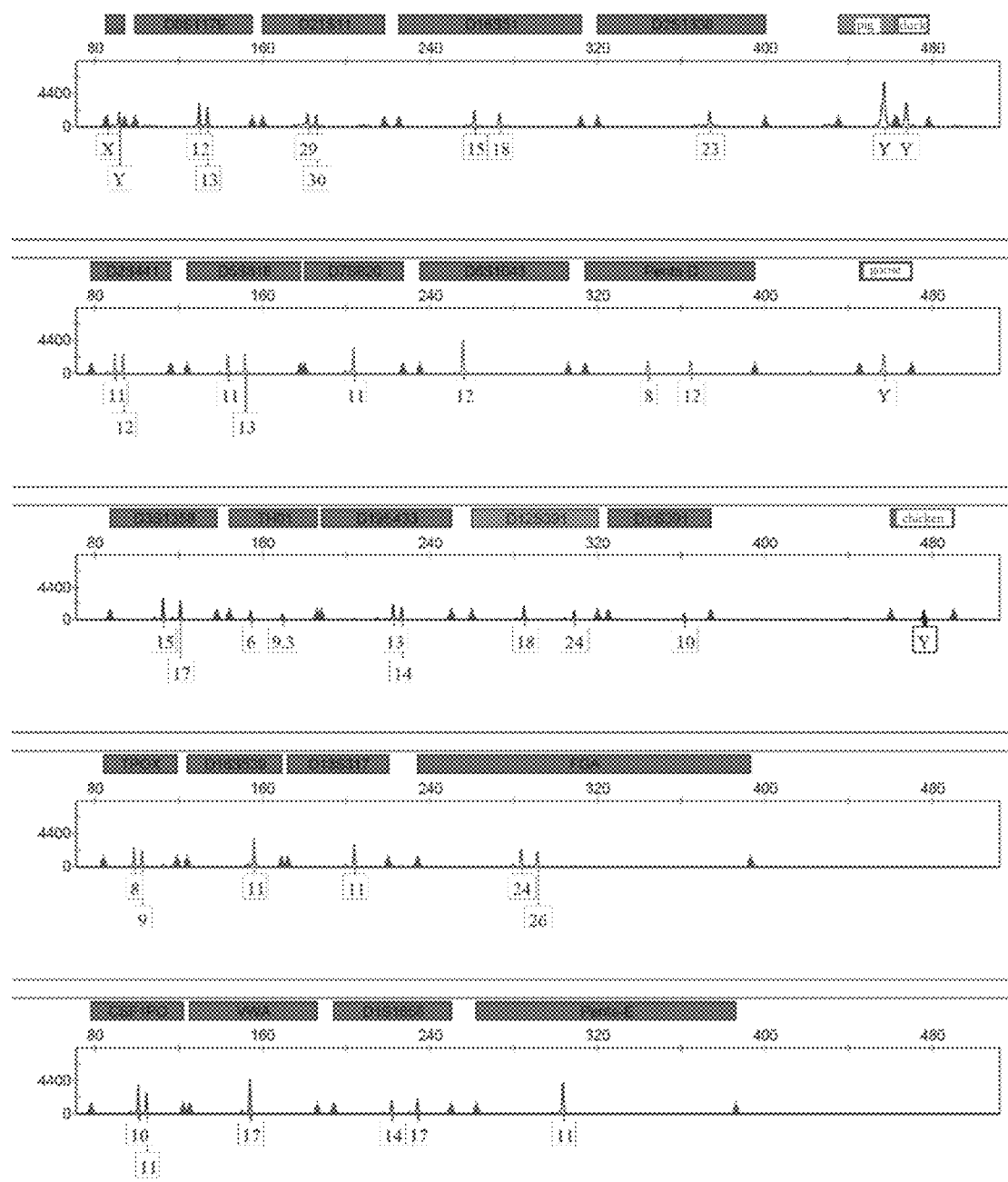
FIG. 6 illustrates a diagram of the amplification results of a mixed sample of the DNAs extracted from chickens, ducks, geese and pigs with Control DNA 9948 at the same concentrations.

As described above, the present invention provides a multiplex PCR amplification method for identifying an unknown biological sample suspected to be from human, which comprises the steps of:
1) collecting an unknown biological sample to be detected, which is suspected to be from human;

2) adding the unknown biological sample to be detected directly, or the nucleic acid extracted from the unknown biological sample to be detected, into premixed PCR reagents;
3) performing multiplex PCR amplification by running PCR amplification procedures;
4) detecting and analyzing PCR amplification products;

wherein the premixed PCR reagents comprise primers specific for human DNA genetic markers and primers specific for nuclear genes on the chromosomes of non-human species.

According to the method described herein, the unknown biological sample refers to a biological sample from which species it is derived is unknown.

In a specific embodiment according to the method of the present invention, the PCR amplification products are detected and analyzed using capillary gel electrophoresis and fluorescence assay. This greatly simplifies the process of the detection and shortens the required time. In a preferred embodiment, the PCR amplification products are detected and analyzed using capillary gel electrophoresis and fluorescence assay with 6 optical wavelengths.

The term "DNA genetic marker" as used in the method of the present invention refers to inheritable and detectable DNA sequences that represent the genetic make-up of an organism and are distributed in a population-characteristic pattern.

According to the method of the present invention, the human DNA genetic markers include human STR loci, gender recognition sites, InDel sites, and/or SNP sites.

In one embodiment, the human DNA genetic markers are human STR loci and gender recognition sites; wherein the human STR loci include STR loci on human autosomes and sex chromosomes.

In another specific embodiment, the human DNA genetic markers include the following 22 human STR loci: D3S1358, TH01, D21S11, D18S51, Penta E, D12S391, D6S1043, D2S1338, D1S1656, D5S818, D13S317, D7S820, D19S433, CSF1PO, Penta D, vWA, D8S1179, TPOX, FGA, D2S441, D16S539 and DYS391, as well as a gender recognition site Amel (non-STR locus).

According to the method of the present invention, the non-human species are non-human mammals, including but not limited to, non-human primates, cats, dogs, sheep, goats, horses, cow, pigs, and rodents (including but not limited to mice and rats); and non-mammals, including but not limited to birds, domestic poultry, reptiles, and amphibians. In a specific embodiment, the non-human species are chickens, ducks, geese and pigs.

According to the method of the present invention, the sample to be detected is selected from blood, blood stains, semen, saliva, body fluids, hair, muscles, or tissues and organs. In some embodiments, the method of the present invention can also be performed directly by amplifying tested materials such as filter paper, FTA cards, cotton pads, and oral swabs.

In the present invention, non-human species are identified by aligning the nucleotide sequences of the same genes among different species and designing species-specific primers and/or probes at locations where the sequences are different to achieve rapid detection and identification of different non-human species. In particular, the genes useful for the identification of non-human species may be all the genes that are present on chromosomes of all the species to be identified but are somewhat different in their nucleotide sequences, such as housekeeping genes on chromosomes, including genes encoding tubulin, ATP synthase, glycolytic enzymes, ribosomal proteins, etc. Preferably, the housekeeping gene used herein is ATP5B gene. Nuclear genes on chromosomes that are suitable for use in the present invention can ensure that the copy number of nucleic acids in the detected sample is independent of different tissue sources, different life cycles or the like. Preferred housekeeping gene sequences are relatively conservative and stable in genetic evolution, and have significant difference among different species while little difference in the same category of species; they have high species-specificity.

In some embodiments according to the method of the present invention, the primers have the following sequences:
Amel: SEQ ID NO: 1-2;
D8S1179: SEQ ID NO: 3-4;
D21S11: SEQ ID NO: 5-6;
D18S51: SEQ ID NO: 7-8;
D2S1338: SEQ ID NO: 9-10;
Pig ATP5B: SEQ ID NO: 11-12;
Duck ATP5B: SEQ ID NO: 13-14;
D2S441: SEQ ID NO: 15-16;
D5S818: SEQ ID NO: 17-18;
D7S820: SEQ ID NO: 19-20;
D6S1043: SEQ ID NO: 21-22;
Penta D: SEQ ID NO: 23-24;
Goose ATP5B: SEQ ID NO: 25-26;
D3S1358: SEQ ID NO: 27-28;
TH01: SEQ ID NO: 29-30;
D19S433: SEQ ID NO: 31-32;
D12S391: SEQ ID NO: 33-34;
Chicken ATP5B: SEQ ID NO: 35-36;
DYS391: SEQ ID NO: 37-38;
TPOX: SEQ ID NO: 39-40;
D16S539: SEQ ID NO: 41-42;
D13S317: SEQ ID NO: 43-44;
FGA: SEQ ID NO: 45-46;
CSF 1PO: SEQ ID NO: 47-48;
vWA: SEQ ID NO: 49-50;
D1S1656: SEQ ID NO: 51-52;
Penta E: SEQ ID NO: 53-54.

In another specific embodiment according to the method of the present invention, the primers are used at the following concentrations:
SEQ ID NO: 1-2: 0.84 µM;
SEQ ID NO: 3-4: 0.5 µM;
SEQ ID NO: 5-6: 0.67 µM;
SEQ ID NO: 7-8: 0.66 µM;
SEQ ID NO: 9-10: 0.67 µM;
SEQ ID NO: 11-12: 0.54 µM;
SEQ ID NO: 13-14: 1.26 µM;
SEQ ID NO: 15-16: 0.3 µM;
SEQ ID NO: 17-18: 0.7 µM;
SEQ ID NO: 19-20: 1.36 µM;
SEQ ID NO: 21-22: 0.5 µM;
SEQ ID NO: 23-24: 0.6 µM;
SEQ ID NO: 25-26: 0.65 µM;
SEQ ID NO: 27-28: 1.3 µM;
SEQ ID NO: 29-30: 1.2 µM;
SEQ ID NO: 31-32: 1.3 µM;
SEQ ID NO: 33-34: 0.65 µM;
SEQ ID NO: 35-36: 4.6 µM;
SEQ ID NO: 37-38: 1.8 µM;
SEQ ID NO: 39-40: 2.7 µM;
SEQ ID NO: 41-42: 1.9 µM;
SEQ ID NO: 43-44: 1.5 µM;
SEQ ID NO: 45-46: 2.0 µM;
SEQ ID NO: 47-48: 2.7 µM;
SEQ ID NO: 49-50: 1.9 µM;

SEQ ID NO: 51-52: 2.0 µM;
SEQ ID NO: 53-54: 1.9 µM.

The present invention further provides a multiplex PCR amplification kit for identifying species and human individuals on an unknown biological sample suspected to be from human, which is characterized in comprising primers specific for human DNA genetic markers and primers specific for nuclear genes on the chromosomes of non-human species. In some embodiments, the human DNA genetic markers include human STR loci, gender recognition sites, InDel sites and/or SNP sites; preferably, the human DNA genetic markers are human STR loci and gender recognition sites.

In some embodiments, the nuclear genes on the chromosomes of non-human species include all the genes that are present on chromosomes of all the species to be identified but are somewhat different in their nucleotide sequences. Preferably, the nuclear genes are housekeeping genes on chromosomes; more preferably, the housekeeping genes include genes encoding tubulin, ATP synthase, glycolytic enzymes, and/or ribosomal proteins; most preferably, the housekeeping gene is ATP5B gene.

In a specific embodiment, the kit comprises primers for amplifying the following human DNA genetic markers and housekeeping genes on the chromosomes of non-human species: D3S1358, TH01, D21S11, D18S51, Penta E, D12S391, D6S1043, D2S1338, D1S1656, D5S818, D13S317, D7S820, D19S433, CSF1PO, Penta D, vWA, D8S1179, TPOX, FGA, D2S441, D16S539, DYS391, and Amel as well as chicken ATP5B, duck ATP5B, goose ATP5B and pig ATP5B.

In a particularly specific embodiment, the primers have the following sequences:
Amel: SEQ ID NO: 1-2;
D8S1179: SEQ ID NO: 3-4;
D21S11: SEQ ID NO: 5-6;
D18S51: SEQ ID NO: 7-8;
D2S1338: SEQ ID NO: 9-10;
Pig ATP5B: SEQ ID NO: 11-12;
Duck ATP5B: SEQ ID NO: 13-14;
D2S441: SEQ ID NO: 15-16;
D5S818: SEQ ID: NO: 17-18;
D7S820: SEQ ID NO: 19-20;
D6S1043: SEQ ID NO: 21-22;
Penta D: SEQ ID NO: 23-24;
goose ATP5B: SEQ ID NO: 25-26;
D3S1358: SEQ ID NO: 27-28;
TH01: SEQ ID NO: 29-30;
D19S433: SEQ ID NO: 31-32;
D12S391: SEQ ID NO: 33-34;
Chicken ATP5B: SEQ ID NO: 35-36;
DYS391: SEQ ID NO: 37-38;
TPOX: SEQ ID NO: 39-40;
D16S539: SEQ ID NO: 41-42;
D13S317: SEQ ID NO: 43-44;
FGA: SEQ ID NO: 45-46;
CSF1PO: SEQ ID NO: 47-48;
vWA: SEQ ID NO: 49-50;
D1S1656: SEQ ID NO: 51-52;
Penta E: SEQ ID NO: 53-54.

In another specific embodiment, the primers are used at the following concentrations:
SEQ ID NO: 1-2: 0.84 µM;
SEQ ID NO: 3-4: 0.5 µM;
SEQ ID NO: 5-6: 0.67 µM;
SEQ ID NO: 7-8: 0.66 µM;
SEQ ID NO: 9-10: 0.67 µM;
SEQ ID NO: 11-12: 0.54 µM;
SEQ ID NO: 13-14: 1.26 µM;
SEQ ID NO: 15-16: 0.3 µM;
SEQ ID NO: 17-18: 0.7 µM;
SEQ ID NO: 19-20: 1.36 µM;
SEQ ID NO: 21-22: 0.5 µM;
SEQ ID NO: 23-24: 0.6 µM;
SEQ ID NO: 25-26: 0.65 µM;
SEQ ID NO: 27-28: 1.3 µM;
SEQ ID NO: 29-30: 1.2 µM;
SEQ ID NO: 31-32: 1.3 µM;
SEQ ID NO: 33-34: 0.65 µM;
SEQ ID NO: 35-36: 4.6 µM;
SEQ ID NO: 37-38: 1.8 µM;
SEQ ID NO: 39-40: 2.7 µM;
SEQ ID NO: 41-42: 1.9 µM;
SEQ ID NO: 43-44: 1.5 µM;
SEQ ID NO: 45-46: 2.0 µM;
SEQ ID NO: 47-48: 2.7 µM;
SEQ ID NO: 49-50: 1.9 µM;
SEQ ID NO: 51-52: 2.0 µM;
SEQ ID NO: 53-54: 1.9 µM.

In addition to the primers listed above, the kit of the present invention further comprises nuclease-free water, PCR reaction mixture, primer mixture, allele mixture, and internal standard SIZE-500 Plus as components. It is worth mentioning that the PCR reaction mixture as used herein has been subject to a series of optimization experiments so as to afford a product that is compatible with all the ordinary tested sample materials available on the Chinese market, including whatman FTA cards, whatman saliva cards, blood filter paper, Bokun FTA cards, Bokun saliva cards, hair, exfoliated cells from the oral cavity, extracted DNAs and the like. Moreover, such an improved buffer can greatly increase the amplification efficiency, effectively shorten the time for terminal adenylation of products and the overall amplification duration, and improve the amplification efficiency of longer fragments and the uniformity of the product. The PCR reaction mixture comprises the following main components: DMSO, Tris-buffer, potassium chloride, ammonium sulfate, dNTP, Tween 20 and betaine.

The present invention will be further described in detail in the following examples in conjunction with the accompanying drawings.

EXAMPLE 1

Determination of Non-Human Species and Specific-sequences

In the practical identification application, contamination by non-human species is primarily caused by ordinary animals in urban and rural areas. Thus, four ordinary non-human species (namely, chickens, ducks, geese and pigs) that are readily available are selected for use in the present application. Sequences of the same gene in each species are selected from the database of NCBI as the detected sequence. By aligning these sequences, a specific region on ATP5B is selected and experimentally verified.

EXAMPLE 2

Determination of Genetic Markers of Human Chromosomal DNAs

In the present invention, the following 22 human chromosomal STR loci are determined by screening: D3S1358, TH01, D21S11, D18S51, Penta E, D12S391, D6S1043, D2S1338, D1S1656, D5S818, D13S317, D7S820, D19S433, CSF1PO, Penta D, vWA, D8S1179, TPOX, FGA, D2S441, D16S539 and DYS391, as well as a gender recognition site Amel (non-STR locus); wherein DYS391, a core site in the China National GeneBank DataBase and a gender recognition site located on chromosome Y, is used for auxiliary sex determination.

EXAMPLE 3

Design of a Combined Scheme of Fluorescently-Labeled Multiplex Amplification System Six-color fluorescent labels (namely, blue, green, yellow, red, purple, and orange labels) were selected for use in the present invention after discriminating and screening fluorescent dyes to construct a combined scheme of six-color fluorescence. When the combined scheme of six-color fluorescence had been determined, the combination of loci and types of the fluorescent labels were designed through numerous repeated experiments. Based on the production costs and the amplification efficiency of the primers for each locus, the above loci were divided into five groups:

the first group: Amel, D8S1179, D21S11, D18S51, D2S1338, pig and duck ATP5B-specific regions, using FAM labels;
the second group: D2S441, D5S818, D7S820, D6S1043, Penta D and a goose ATP5B-specific region, using HEX labels;
the third group: D3S1358, TH01, D19S433, D12S391, DYS391 and a chicken ATP5B-specific region, using TAM labels;
the fourth group: TPOX, D16S539, D13S317 and FGA, using ROX labels; and
the fifth group: CSF1PO, vWA, D1S1656 and Penta E, using Alex 594 labels; and orange fluorescent label (i.e., Atto633) is selected for internal standard.

Specific primers were first designed at regions flanking repeated sequences of the 23 loci described above using Primer Premier5 software. The annealing temperature for each primer was around 60° C. No primer dimers, other interactions or cross-reactions would be present. The amplification product has a length ranging from 70 to 500 bp. Each pair of primers was assayed for amplification and optimized until a clear single band was observed after amplification.

Secondly, as to non-human species, ATP5B gene was selected by searching the gene library, which expresses beta polypeptide of F1 complex of ATP synthase. Specific portion of DNA in the gene was selected by aligning the DNA sequences of the same gene from different species using DNAMAN. Specific primers were designed using the Primer Premier5. No primer dimer, other interactions or cross-reactions would be present. After amplification, there was a clear single band for the target species. Multiplex amplification was optimized and validated for different species. No non-specific amplification peaks for other species than the target species, especially no interference peaks for pure human DNA, would occur.

Each locus was separated by the lengths of the fragments amplified by the primers in each of the above groups; and sequences of the primer were optimized so that no non-specific band was present within the amplification range to ensure high-efficient detection. Simultaneously, detection was performed on different species to ensure high species specificity. Subsequently, the concentrations of the primers were adjusted such that accurate STR typing on human samples and specific detection on non-human species are possible at 0.125 ng of positive control samples from both human and non-human species; and the heights of amplification peak of the same color remained 50% or higher at equal amounts of the DNAs of the human and non-human species. Sequences and concentrations of the specific primers used are shown in Table 1 below:

TABLE 1

Sequences and concentrations of primers corresponding to the respective tested sites

| Locus | Primer sequence | Concentration | Serial No. of the primer sequence |
| --- | --- | --- | --- |
| Amel | CCCTGGGCTCTGTAAAGAATAG | 0.84 µM | SEQ ID NO: 1 |
| | ACTGGTGGTAGGAACTGTAAA | 0.84 µM | SEQ ID NO: 2 |
| D8S1179 | GCCACACGGCCTGGCAACTTA | 0.5 µM | SEQ ID NO: 3 |
| | GTCCTGTAGATTATTTTCACTGTGG | 0.5 µM | SEQ ID NO: 4 |
| D21S11 | AGGAGGTAGATAGACTGGATAGATAG | 0.67 µM | SEQ ID NO: 5 |
| | CTCAATTCCCCAAGTGAATTGCC | 0.67 µM | SEQ ID NO: 6 |
| D18S51 | GCTGTAGTCTCAGCTACTTGC | 0.66 µM | SEQ ID NO: 7 |
| | GACTGGTGTGTGGAGATGTCTTA | 0.66 µM | SEQ ID NO: 8 |
| D2S1338 | TTCTTCCCTGTCTCACCCCTTTCC | 0.67 µM | SEQ ID NO: 9 |
| | CGAGTGGAGGTGCCTAAAGACTTCAT | 0.67 µM | SEQ ID NO: 10 |
| Pig | CAATCTAAAAGTTTCACTTAGAGTCC | 0.54 µM | SEQ ID NO: 11 |
| | CAATAGGAGCTGTAGCCACCGACCTA | 0.54 µM | SEQ ID NO: 12 |
| Duck | GGTTTTCAAGCGCTCGGATGC | 1.26 µM | SEQ ID NO: 13 |
| | ACCTCCGAATAAACCTGGGG | 1.26 µM | SEQ ID NO: 14 |
| D2S441 | GAACTGTGGCTCATCTATGAAA | 0.3 µM | SEQ ID NO: 15 |
| | GCTAAGTGGCTGTGGTGTTATGATA | 0.3 µM | SEQ ID NO: 16 |
| D5S818 | CATAGCCACAGTTTACAACATTTGTAT | 0.7 µM | SEQ ID NO: 17 |
| | TGACAAGGGTGATTTTCCTCTTTGGT | 0.7 µM | SEQ ID NO: 18 |

TABLE 1-continued

Sequences and concentrations of primers corresponding to the respective tested sites

| Locus | Primer sequence | Concentration | Serial No. of the primer sequence |
|---|---|---|---|
| D7S820 | GTAAGAATTATAACGATTCCACATTTAT | 1.36 µM | SEQ ID NO: 19 |
| | TATAAAGGGTATGATAGAACACTTGTCA | 1.36 µM | SEQ ID NO: 20 |
| D6S1043 | GTGCTTACAGATGGCATATTGTGAAA | 0.5 µM | SEQ ID NO: 21 |
| | GCCCACTTCTAAAACACCTCTAATGTT | 0.5 µM | SEQ ID NO: 22 |
| Panta D | GAAGTGAGCCATGATCACACCACT | 0.6 µM | SEQ ID NO: 23 |
| | TAGAAGTACTTTCTCTTAGCCTGT | 0.6 µM | SEQ ID NO: 24 |
| Goose | GAGCAGCTGAGTGGCCAAATCC | 0.65 µM | SEQ ID NO: 25 |
| | AGCTCGAGGGCACTGCGGTAAA | 0.65 µM | SEQ ID NO: 26 |
| D3S1358 | CAAATCAACAGAGGCTTGCATGT | 1.3 µM | SEQ ID NO: 27 |
| | GTGACAGAGCAAGACCCTGTCTC | 1.3 µM | SEQ ID NO: 28 |
| TH01 | CCGATTATCCAGCCTGGCC | 1.2 µM | SEQ ID NO: 29 |
| | GGCTCTGGGGTGATTCCCATT | 1.2 µM | SEQ ID NO: 30 |
| D19S433 | TGTTGGTTACATGAATAAGTTCTTTA | 1.3 µM | SEQ ID NO: 31 |
| | TGAGGCTGCAAAAAGCTATAATTG | 1.3 µM | SEQ ID NO: 32 |
| D12S391 | CAGGGAAGATGAAAAAAGAGACTGT | 0.65 µM | SEQ ID NO: 33 |
| | GATTTTGGCTTTTAGACCTGGACTG | 0.65 µM | SEQ ID NO: 34 |
| Chicken | GCTCATCTCTACAAACTCAGGGGCTT | 4.6 µM | SEQ ID NO: 35 |
| | CTATTTCCCTGCACCGTTTTGTCCT | 4.6 µM | SEQ ID NO: 36 |
| DYS391 | CAGCCCTGGGATCCTGCTCA | 1.8 µM | SEQ ID NO: 37 |
| | GAATAAAATCTCCCTGGTTGCAAGCA | 1.8 µM | SEQ ID NO: 38 |
| TPOX | CAGAACAGGCACTTAGGGA | 2.7 µM | SEQ ID NO: 39 |
| | GCTTTCTGTCCTTGTCAGCGTTTAT | 2.7 µM | SEQ ID NO: 40 |
| D16S539 | AGATCCCAAGCTCTTCCTCTT | 1.9 µM | SEQ ID NO: 41 |
| | CTGTGTGCATCTGTAAGCATG | 1.9 µM | SEQ ID NO: 42 |
| D13S317 | TCAAATCTCCTCCTTCAACTTG | 1.5 µM | SEQ ID NO: 43 |
| | GAGTTCATTTCTTTAGTGGGCATC | 1.5 µM | SEQ ID NO: 44 |
| FGA | ACTTCAATTCTGCTTCTCAGATC | 2.0 µM | SEQ ID NO: 45 |
| | ACTCACAGATTAAACTGTAACCAAAATA | 2.0 µM | SEQ ID NO: 46 |
| CSF1PO | CTGCCTTCATAGATAGAAGATAGATA | 2.7 µM | SEQ ID NO: 47 |
| | CTCAGACCCTGTTCTAAGTACTTC | 2.7 µM | SEQ ID NO: 48 |
| vWA | GTGGATGATAAGAATAATCAGTATGTG | 1.9 µM | SEQ ID NO: 49 |
| | ATTTTGGACAGATGATAAATACATAGGATG | 1.9 µM | SEQ ID NO: 50 |
| D1S1656 | GATTCTCCTTCAGTCCTGTGTTAGTCA | 2.0 µM | SEQ ID NO: 51 |
| | GGTGGTAGAGATGGAAGAAAATC | 2.0 µM | SEQ ID NO: 52 |
| Panta E | GATGTGTGTAAAGTGCTTAGTATCATGAT | 2.0 µM | SEQ ID NO: 53 |
| | TGAAAAATTAGCTGGGTGTGGTGGT | 2.0 µM | SEQ ID NO: 54 |

EXAMPLE 4

Experimental Procedures for Amplifying the Tested Sites and Detecting Their Products The multiplex PCR amplification kit for identifying species and human individuals on an unknown biological sample suspected to be from human as provided herein comprises:
1) PCR Master Mix;
2) Primer Mix;
3) Control DNA 9948A;
4) Allelic Ladder allelic genotyping standard;
5) SIZE-500 Plus orange fluorescent molecular weight internal standard;
6) Spectral calibration standards.

The above PCR Master comprises: 6-10 mM DMSO, 80-125 mM Tris-buffer, 100-125 mM potassium chloride, 50-65 mM ammonium sulfate, 6-9 mM deoxynucleotide triphosphate (dATP, dGTP, dTTP, dCTP), 1.5-3 mg/mL BSA, 1.5-2% Tween 20, and 0.2-2M betaine, and is compatible with various testing materials that have been commonly used for amplification and available on the market.

The above Primer Mix comprises all the primers for amplifying 27 detection sites (their concentrations are shown in Table 1), 2-4 U/25 μl-reaction Taq polymerase, 6-8 mM magnesium chloride, etc.

The above Control DNA 9948A is human genomic DNA, purchased from Suzhou Xinhai Biotechnology Co., Ltd.

The above Allelic Ladder allelic genotyping standard is a collection of the distribution of each allele having all the different genotypes at the above-mentioned loci in certain numbers of populations.

The above SIZE-500Plus orange fluorescent molecular weight internal standard is a series of amplification products used to calibrate certain fragment sizes.

The above spectral calibration standards are fluorescent PCR amplification products of 6 fragments having different sizes.

1. Configuration of the reaction system

| Component | Volume |
|---|---|
| nuclease-free water (RNase/DNase-free ultrapure water) | Added to a final volume of 25.0 μL |
| PCR Master Mix | 12.5 μL |
| Primer Mix | 6.25 μL |
| Control DNA 9948A/an unknown biological sample | 0.125-2 ng |
| Total | 25 μL |

2. Experimental protocol for thermocycler amplification

1) Placing the PCR amplification tube on the thermocycler;
2) Performing the amplification by selecting the procedures as recommended below;
3) Keeping the amplified samples away from light.

| Step | Temperature | Duration |
|---|---|---|
| 1 | 95° C. | 2-10 min |
| 2 | 94° C. | 5-10 s |
| 3 | 60° C.~63° C. | 60-90 s |
| 4 | 70° C. | 30-60 s |
| 5 | N/A | Repeating steps 2-4, 27-30 times (28-32 times in total) |
| 6 | 60° C. | 10-30 min |
| 7 | 4° C. | Continued until the PCR product was recovered |

3. Fluorescence assay of the amplification products on genetic analyzer

A loading mixture (25-50 μL SIZE-500 Plus+1000 μL deionized formamide) was prepared from deionized formamide and the molecular weight internal standard (SIZE-500 Plus) in the system. 9 μL of the loading mixture was blended with 1 μL of the amplification product or allelic genotyping standard in the system (Allelic ladder). Air bubbles should be avoided and electrophoresis was carried out as soon as possible. The amplification product was detected and analyzed using a genetic analyzer (such as ABI 3500/3130 series). The data obtained after electrophoresis were analyzed on GeneMapper ID-X data analysis software to obtain genotyping spectrum and data.

EXAMPLE 5

Sensitivity and Specificity Analysis of the Assay Kit

Sensitivity analysis: After the positive control was diluted according to certain copy number fold, it was assayed by PCR amplification and capillary electrophoresis until no signal was detected. This copy number was considered as the lowest detection limit, i.e., the sensitivity of the kit. The highest sensitivity refers to the sensitivity when DNA samples at a concentration as low as 0.125 ng can be detected.

Specificity analysis: Control DNA 9948, chicken, duck, goose, pig, dog, sheep, mouse, cow, E. coli and the like were assayed with fluorescently-labeled multiplex amplification and validation system at 27 tested sites according to the present invention. For the Control DNA 9948, only human STR loci were observed; for the chicken, duck, goose, and pig, only the corresponding specific peaks were observed; and for the rest of the species, no specific amplification peak was observed, indicating that this system has high specificity for the identification of species.

EXAMPLE 6

Figure 7:
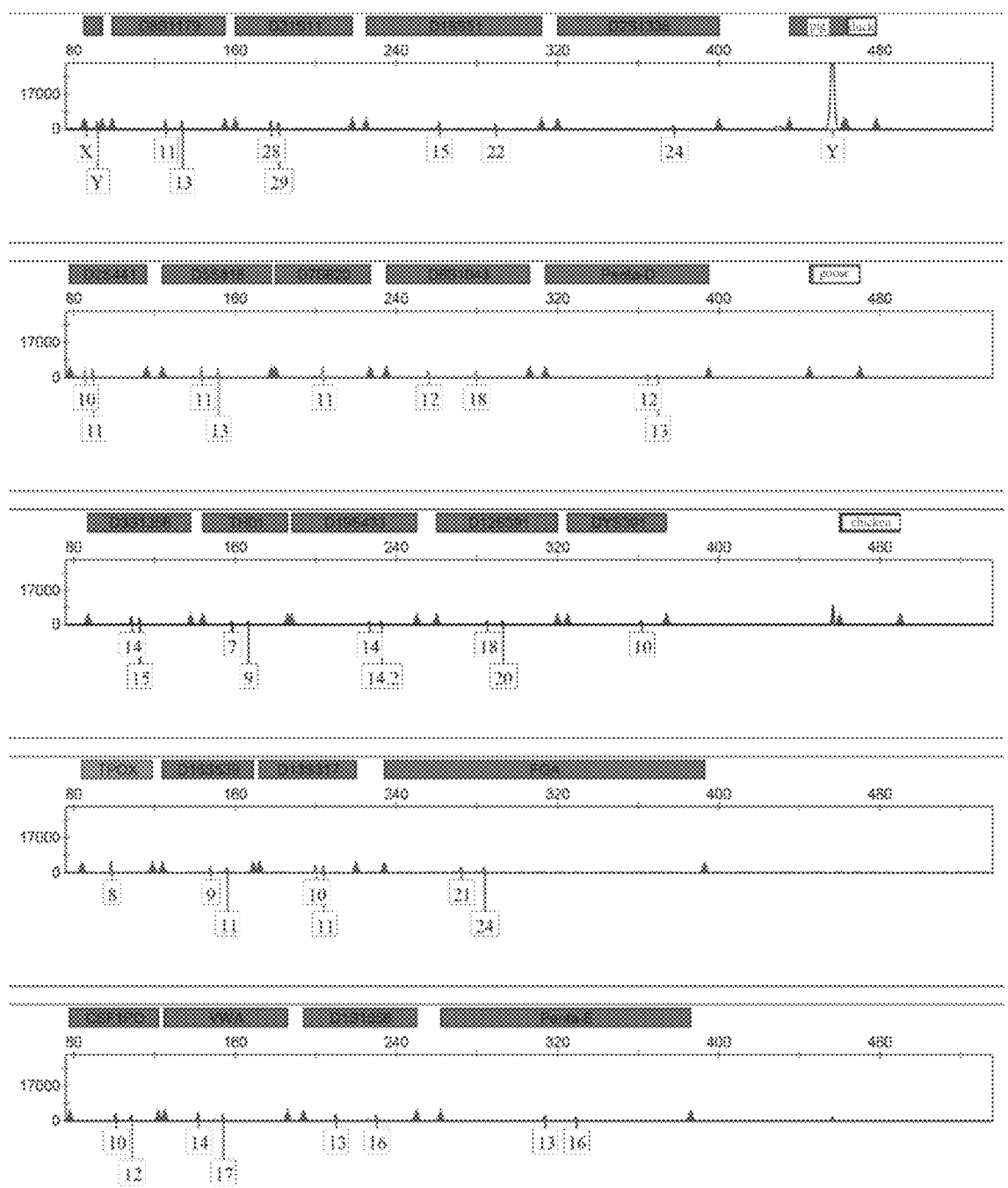
FIG. 7 illustrates a diagram of the amplification results of the DNAs extracted from an unknown sample.

Application of the Method According to the Present Invention in Samples Derived from Unknown Sources The kit provided by the method of the present invention is used for detecting samples from unknown sources. The detection steps are described as follows:

1. Collecting a sample of blood stain from an unknown source, which was provided by certain University;
2. Processing the tested material: the tested material used in this case was the sample extracted via Chelex, and 2 μL of the sample was used as an assay template;
3. Amplification and detection: Fluorescent labeling, PCR amplification and detection with a genetic analyzer were performed according to Examples 2 to 5, using the kit of the present invention. The detection results were shown in FIG. 7 and listed in the following Table 3:

TABLE 3

Detection results of a sample from unknown source obtained by using the method and kit according to the present invention

| Tested sites | Detection results |
|---|---|
| Amel | X/Y |
| D8S1179 | 11/13 |
| D21S11 | 28/29 |
| D18S51 | 15/22 |
| D2S1338 | 24/24 |
| Pig ATP5B | Y |
| Duck ATP5B | — |
| D2S441 | 10/11 |
| D5S818 | 11/13 |
| D7S820 | 11/11 |
| D6S1043 | 12/18 |
| PantaD | 12/13 |
| Goose ATP5B | — |
| D3S1358 | 14/15 |
| TH01 | 7/9 |
| D19S433 | 14/14.2 |
| D12S391 | 18/20 |
| Chicken ATP5B | — |
| DYS391 | 10 |
| TPOX | 8/8 |

TABLE 3-continued

Detection results of a sample from unknown source obtained by using the method and kit according to the present invention

| Tested sites | Detection results |
|---|---|
| D16S539 | 9/11 |
| D13S317 | 10/11 |
| FGA | 21/24 |
| CSF1PO | 10/12 |
| vWA | 14/17 |
| D1S1656 | 13/16 |
| PantaE | 13/16 |

The results show that the sample from unknown source contains a small amount of human DNA and is also blended with a large amount of porcine DNA.

In conclusion, by screening and validating specific nuclear gene sequences among different species, combining the identification of one or more non-human species with multiplex amplification and detection of human chromosomal STRs, the present invention can accurately acquire information of the sample in a single assay when a sample from unknown source (which is non-human DNA or is blended with non-human DNA) is subjected to the detection of STRs without changing or complicating the procedures of assay. In forensic identification, it is possible to help the person who handles the case to rapidly identify whether a sample is of human origin or whether a sample is contaminated by DNAs of other species. Moreover, approximate content proportions of the DNAs from different species in the sample can be determined based on the heights of the detection peaks, and such information will assist the person in making a quicker and more accurate assessment when higher DNA concentrations are observed and the detected typing results are undesirable. In the case where samples are contaminated by non-human species, it is possible to check the emergence of the non-specific peaks for different species by synchronously taking reference to the species/genus-specificity reports provided by the manufactures of STR reagents so as to accurately recognize actual target peaks of human STRs. Thus, the method according to the present invention can significantly increase the accuracy of result determination by less repeated tests or validation procedures using reduced consumption of DNA samples (especially those containing small amounts of DNA), and thus significantly increase the efficiency of forensic identification.

The illustrations described above should not be construed as limitations on the method and application of the present invention; and the present invention will not be limited thereto. Variations, modifications, additions or replacements that can be contemplated by those of ordinary skills in the art within the substantive scope according to the method of the present invention should also fall within the protection scope of the present invention.

What is claimed is:

1. A multiplex PCR amplification method for identifying an unknown biological sample suspected to be from human, the method comprising the steps of:
   (a) collecting an unknown biological sample to be detected, which is suspected to be from human;
   (b) adding the unknown biological sample or nucleic acids extracted from the unknown biological sample into premixed PCR reagents; wherein the premixed PCR reagents comprise primers specific for human DNA genetic markers and primers specific for ATP5B gene of non-human species, wherein the primers comprise SEQ ID NO 1-54;
   (c) performing multiplex PCR amplification of the sample and the PCR reagents from step (b); and
   (d) detecting and analyzing the PCR amplification products to identify the biological sample.

2. The method according to claim 1, wherein the step of detecting and analyzing the PCR amplification products comprises identifying differences in the sizes of the PCR amplification products and/or conducting sequencing analysis on the sequences of the PCR amplification products.

3. The method according to claim 2, wherein the PCR amplification products are detected and analyzed by identifying differences in the sizes of the PCR amplification products, using methods selected from the group consisting of polyacrylamide gel electrophoresis, agarose gel electrophoresis, microfluidic chip, capillary gel electrophoresis and fluorescent assay.

4. The method according to claim 1, wherein the human DNA genetic markers include human STR loci, gender recognition sites, InDel sites, and/or SNP sites.

5. The method according to claim 4, wherein the human DNA genetic markers include the following 22 human STR loci: D3S1358, TH01, D21S11, D18S51, Penta E, D12S391, D6S1043, D2S1338, D1S1656, D5S818, D13S317, D7S820, D19S433, CSF1PO, Penta D, vWA, D8S1179, TPOX, FGA, D2S441, D16S539 and DYS391, as well as a gender recognition site Amel, which is not STR locus.

6. The method according to claim 1, wherein the non-human species are chickens, ducks, geese and pigs.

7. The method according to claim 1, wherein the primers are used at the following concentrations:

SEQ ID NO: 1-2: 0.84 µM;
SEQ ID NO: 3-4: 0.5 µM;
SEQ ID NO: 5-6: 0.67 µM;
SEQ ID NO: 7-8: 0.66 µM;
SEQ ID NO: 9-10: 0.67 µM;
SEQ ID NO: 11-12: 0.54 µM;
SEQ ID NO: 13-14: 1.26 µM;
SEQ ID NO: 15-16: 0.3 µM;
SEQ ID NO: 17-18: 0.7 µM;
SEQ ID NO: 19-20: 1.36 µM;
SEQ ID NO: 21-22: 0.5 µM;
SEQ ID NO: 23-24: 0.6 µM;
SEQ ID NO: 25-26: 0.65 µM;
SEQ ID NO: 27-28: 1.3 µM;
SEQ ID NO: 29-30: 1.2 µM;
SEQ ID NO: 31-32: 1.3 µM;
SEQ ID NO: 33-34: 0.65 µM;
SEQ ID NO: 35-36: 4.6 µM;
SEQ ID NO: 37-38: 1.8 µM;
SEQ ID NO: 39-40: 2.7 µM;
SEQ ID NO: 41-42: 1.9 µM;
SEQ ID NO: 43-44: 1.5 µM;
SEQ ID NO: 45-46: 2.0 µM;
SEQ ID NO: 47-48: 2.7 µM;
SEQ ID NO: 49-50: 1.9 µM;
SEQ ID NO: 51-52: 2.0 µM; and
SEQ ID NO: 53-54: 1.9 µM.

* * * * *

SEQUENCE LISTING

```
<160> NUMBER OF SEQ ID NOS: 54

<210> SEQ ID NO 1
<211> LENGTH: 22
<212> TYPE: DNA
<213> ORGANISM: Artificial Sequence
<220> FEATURE:
<223> OTHER INFORMATION: Primer 1 for Amel

<400> SEQUENCE: 1
ccctgggctc tgtaaagaat ag                                              22

<210> SEQ ID NO 2
<211> LENGTH: 21
<212> TYPE: DNA
<213> ORGANISM: Artificial Sequence
<220> FEATURE:
<223> OTHER INFORMATION: Primer 2 for Amel

<400> SEQUENCE: 2
actggtggta ggaactgtaa a                                               21

<210> SEQ ID NO 3
<211> LENGTH: 21
<212> TYPE: DNA
<213> ORGANISM: Artificial Sequence
<220> FEATURE:
<223> OTHER INFORMATION: Primer 1 for D8S1179

<400> SEQUENCE: 3
gccacacggc ctggcaactt a                                               21

<210> SEQ ID NO 4
<211> LENGTH: 25
<212> TYPE: DNA
<213> ORGANISM: Artificial Sequence
<220> FEATURE:
```

```
<223> OTHER INFORMATION: Primer 2 for D8S1179

<400> SEQUENCE: 4
gtcctgtaga ttattttcac tgtgg                                              25

<210> SEQ ID NO 5
<211> LENGTH: 26
<212> TYPE: DNA
<213> ORGANISM: Artificial Sequence
<220> FEATURE:
<223> OTHER INFORMATION: Primer 1 for D21S11

<400> SEQUENCE: 5
aggaggtaga tagactggat agatag                                             26

<210> SEQ ID NO 6
<211> LENGTH: 23
<212> TYPE: DNA
<213> ORGANISM: Artificial Sequence
<220> FEATURE:
<223> OTHER INFORMATION: Primer 2 for D21S11

<400> SEQUENCE: 6
ctcaattccc caagtgaatt gcc                                                23

<210> SEQ ID NO 7
<211> LENGTH: 21
<212> TYPE: DNA
<213> ORGANISM: Artificial Sequence
<220> FEATURE:
<223> OTHER INFORMATION: Primer 1 for D18S51

<400> SEQUENCE: 7
gctgtagtct cagctacttg c                                                  21

<210> SEQ ID NO 8
<211> LENGTH: 23
<212> TYPE: DNA
<213> ORGANISM: Artificial Sequence
<220> FEATURE:
<223> OTHER INFORMATION: Primer 2 for D18S51

<400> SEQUENCE: 8
gactggtgtg tggagatgtc tta                                                23

<210> SEQ ID NO 9
<211> LENGTH: 25
<212> TYPE: DNA
<213> ORGANISM: Artificial Sequence
<220> FEATURE:
<223> OTHER INFORMATION: Primer 1 for D2S1338

<400> SEQUENCE: 9
ttcttccctg tctcacccct tttcc                                              25

<210> SEQ ID NO 10
<211> LENGTH: 26
<212> TYPE: DNA
<213> ORGANISM: Artificial Sequence
<220> FEATURE:
<223> OTHER INFORMATION: Primer 2 for D2S1338

<400> SEQUENCE: 10
cgagtggagg tgcctaaaga cttcat                                             26
```

```
<210> SEQ ID NO 11
<211> LENGTH: 26
<212> TYPE: DNA
<213> ORGANISM: Artificial Sequence
<220> FEATURE:
<223> OTHER INFORMATION: Primer 1 for Pig ATP5B

<400> SEQUENCE: 11
caatctaaaa gtttcactta gagtcc                                        26

<210> SEQ ID NO 12
<211> LENGTH: 26
<212> TYPE: DNA
<213> ORGANISM: Artificial Sequence
<220> FEATURE:
<223> OTHER INFORMATION: Primer 2 for Pig ATP5B

<400> SEQUENCE: 12
caataggagc tgtagccacc gaccta                                        26

<210> SEQ ID NO 13
<211> LENGTH: 21
<212> TYPE: DNA
<213> ORGANISM: Artificial Sequence
<220> FEATURE:
<223> OTHER INFORMATION: Primer 1 for Duck ATP5B

<400> SEQUENCE: 13
ggttttcaag cgctcggatg c                                             21

<210> SEQ ID NO 14
<211> LENGTH: 20
<212> TYPE: DNA
<213> ORGANISM: Artificial Sequence
<220> FEATURE:
<223> OTHER INFORMATION: Primer 2 for Duck ATP5B

<400> SEQUENCE: 14
acctccgaat aaacctgggg                                               20

<210> SEQ ID NO 15
<211> LENGTH: 22
<212> TYPE: DNA
<213> ORGANISM: Artificial Sequence
<220> FEATURE:
<223> OTHER INFORMATION: Primer 1 for D2S441

<400> SEQUENCE: 15
gaactgtggc tcatctatga aa                                            22

<210> SEQ ID NO 16
<211> LENGTH: 25
<212> TYPE: DNA
<213> ORGANISM: Artificial Sequence
<220> FEATURE:
<223> OTHER INFORMATION: Primer 2 for D2S441

<400> SEQUENCE: 16
gctaagtggc tgtggtgtta tgata                                         25

<210> SEQ ID NO 17
<211> LENGTH: 27
<212> TYPE: DNA
<213> ORGANISM: Artificial Sequence
<220> FEATURE:
<223> OTHER INFORMATION: Primer 1 for D5S818
```

<400> SEQUENCE: 17
catagccaca gtttacaaca tttgtat                                    27

<210> SEQ ID NO 18
<211> LENGTH: 26
<212> TYPE: DNA
<213> ORGANISM: Artificial Sequence
<220> FEATURE:
<223> OTHER INFORMATION: Primer 2 for D5S818

<400> SEQUENCE: 18
tgacaagggt gattttcctc tttggt                                     26

<210> SEQ ID NO 19
<211> LENGTH: 28
<212> TYPE: DNA
<213> ORGANISM: Artificial Sequence
<220> FEATURE:
<223> OTHER INFORMATION: Primer 1 for D7S820

<400> SEQUENCE: 19
gtaagaatta taacgattcc acatttat                                   28

<210> SEQ ID NO 20
<211> LENGTH: 28
<212> TYPE: DNA
<213> ORGANISM: Artificial Sequence
<220> FEATURE:
<223> OTHER INFORMATION: Primer 2 for D7S820

<400> SEQUENCE: 20
tataaagggt atgatagaac acttgtca                                   28

<210> SEQ ID NO 21
<211> LENGTH: 26
<212> TYPE: DNA
<213> ORGANISM: Artificial Sequence
<220> FEATURE:
<223> OTHER INFORMATION: Primer 1 for D6S1043

<400> SEQUENCE: 21
gtgcttacag atggcatatt gtgaaa                                     26

<210> SEQ ID NO 22
<211> LENGTH: 27
<212> TYPE: DNA
<213> ORGANISM: Artificial Sequence
<220> FEATURE:
<223> OTHER INFORMATION: Primer 2 for D6S1043

<400> SEQUENCE: 22
gcccacttct aaaacacctc taatgtt                                    27

<210> SEQ ID NO 23
<211> LENGTH: 24
<212> TYPE: DNA
<213> ORGANISM: Artificial Sequence
<220> FEATURE:
<223> OTHER INFORMATION: Primer 1 for Penta D

<400> SEQUENCE: 23
gaagtgagcc atgatcacac cact                                       24

<210> SEQ ID NO 24
<211> LENGTH: 24

```
<212> TYPE: DNA
<213> ORGANISM: Artificial Sequence
<220> FEATURE:
<223> OTHER INFORMATION: Primer 2 for Penta D

<400> SEQUENCE: 24
tagaagtact ttctcttagc ctgt                                              24

<210> SEQ ID NO 25
<211> LENGTH: 22
<212> TYPE: DNA
<213> ORGANISM: Artificial Sequence
<220> FEATURE:
<223> OTHER INFORMATION: Primer 1 for Goose ATP5B

<400> SEQUENCE: 25
gagcagctga gtggccaaat cc                                                22

<210> SEQ ID NO 26
<211> LENGTH: 22
<212> TYPE: DNA
<213> ORGANISM: Artificial Sequence
<220> FEATURE:
<223> OTHER INFORMATION: Primer 2 for Goose ATP5B

<400> SEQUENCE: 26
agctcgaggg cactgcggta aa                                                22

<210> SEQ ID NO 27
<211> LENGTH: 23
<212> TYPE: DNA
<213> ORGANISM: Artificial Sequence
<220> FEATURE:
<223> OTHER INFORMATION: Primer 1 for D3S1358

<400> SEQUENCE: 27
caaatcaaca gaggcttgca tgt                                               23

<210> SEQ ID NO 28
<211> LENGTH: 23
<212> TYPE: DNA
<213> ORGANISM: Artificial Sequence
<220> FEATURE:
<223> OTHER INFORMATION: Primer 2 for D3S1358

<400> SEQUENCE: 28
gtgacagagc aagaccctgt ctc                                               23

<210> SEQ ID NO 29
<211> LENGTH: 19
<212> TYPE: DNA
<213> ORGANISM: Artificial Sequence
<220> FEATURE:
<223> OTHER INFORMATION: Primer 1 for TH01

<400> SEQUENCE: 29
ccgattatcc agcctggcc                                                    19

<210> SEQ ID NO 30
<211> LENGTH: 21
<212> TYPE: DNA
<213> ORGANISM: Artificial Sequence
<220> FEATURE:
<223> OTHER INFORMATION: Primer 2 for TH01
```

```
<400> SEQUENCE: 30
ggctctgggg tgattcccat t                                          21

<210> SEQ ID NO 31
<211> LENGTH: 26
<212> TYPE: DNA
<213> ORGANISM: Artificial Sequence
<220> FEATURE:
<223> OTHER INFORMATION: Primer 1 for D19S433

<400> SEQUENCE: 31
tgttggttac atgaataagt tcttta                                     26

<210> SEQ ID NO 32
<211> LENGTH: 24
<212> TYPE: DNA
<213> ORGANISM: Artificial Sequence
<220> FEATURE:
<223> OTHER INFORMATION: Primer 2 for D19S433

<400> SEQUENCE: 32
tgaggctgca aaaagctata attg                                       24

<210> SEQ ID NO 33
<211> LENGTH: 25
<212> TYPE: DNA
<213> ORGANISM: Artificial Sequence
<220> FEATURE:
<223> OTHER INFORMATION: Primer 1 for D12S391

<400> SEQUENCE: 33
cagggaagat gaaaaagag actgt                                       25

<210> SEQ ID NO 34
<211> LENGTH: 25
<212> TYPE: DNA
<213> ORGANISM: Artificial Sequence
<220> FEATURE:
<223> OTHER INFORMATION: Primer 2 for D12S391

<400> SEQUENCE: 34
gattttggct tttagacctg gactg                                      25

<210> SEQ ID NO 35
<211> LENGTH: 26
<212> TYPE: DNA
<213> ORGANISM: Artificial Sequence
<220> FEATURE:
<223> OTHER INFORMATION: Primer 1 for Chicken ATP5B

<400> SEQUENCE: 35
gctcatctct acaaactcag gggctt                                     26

<210> SEQ ID NO 36
<211> LENGTH: 25
<212> TYPE: DNA
<213> ORGANISM: Artificial Sequence
<220> FEATURE:
<223> OTHER INFORMATION: Primer 2 for Chicken ATP5B

<400> SEQUENCE: 36
ctatttccct gcaccgtttt gtcct                                      25

<210> SEQ ID NO 37
```

```
<211> LENGTH: 20
<212> TYPE: DNA
<213> ORGANISM: Artificial Sequence
<220> FEATURE:
<223> OTHER INFORMATION: Primer 1 for DYS391

<400> SEQUENCE: 37
cagccctggg atcctgctca                                               20

<210> SEQ ID NO 38
<211> LENGTH: 26
<212> TYPE: DNA
<213> ORGANISM: Artificial Sequence
<220> FEATURE:
<223> OTHER INFORMATION: Primer 2 for DYS391

<400> SEQUENCE: 38
gaataaaatc tccctggttg caagca                                        26

<210> SEQ ID NO 39
<211> LENGTH: 19
<212> TYPE: DNA
<213> ORGANISM: Artificial Sequence
<220> FEATURE:
<223> OTHER INFORMATION: Primer 1 for TPOX

<400> SEQUENCE: 39
cagaacaggc acttaggga                                                19

<210> SEQ ID NO 40
<211> LENGTH: 25
<212> TYPE: DNA
<213> ORGANISM: Artificial Sequence
<220> FEATURE:
<223> OTHER INFORMATION: Primer 2 for TPOX

<400> SEQUENCE: 40
gctttctgtc cttgtcagcg tttat                                         25

<210> SEQ ID NO 41
<211> LENGTH: 21
<212> TYPE: DNA
<213> ORGANISM: Artificial Sequence
<220> FEATURE:
<223> OTHER INFORMATION: Primer 1 for D16S539

<400> SEQUENCE: 41
agatcccaag ctcttcctct t                                             21

<210> SEQ ID NO 42
<211> LENGTH: 21
<212> TYPE: DNA
<213> ORGANISM: Artificial Sequence
<220> FEATURE:
<223> OTHER INFORMATION: Primer 2 for D16S539

<400> SEQUENCE: 42
ctgtgtgcat ctgtaagcat g                                             21

<210> SEQ ID NO 43
<211> LENGTH: 22
<212> TYPE: DNA
<213> ORGANISM: Artificial Sequence
<220> FEATURE:
<223> OTHER INFORMATION: Primer 1 for D13S317
```

```
<400> SEQUENCE: 43
tcaaatctcc tccttcaact tg                                    22

<210> SEQ ID NO 44
<211> LENGTH: 24
<212> TYPE: DNA
<213> ORGANISM: Artificial Sequence
<220> FEATURE:
<223> OTHER INFORMATION: Primer 2 for D13S317

<400> SEQUENCE: 44
gagttcattt ctttagtggg catc                                  24

<210> SEQ ID NO 45
<211> LENGTH: 23
<212> TYPE: DNA
<213> ORGANISM: Artificial Sequence
<220> FEATURE:
<223> OTHER INFORMATION: Primer 1 for FGA

<400> SEQUENCE: 45
acttcaattc tgcttctcag atc                                   23

<210> SEQ ID NO 46
<211> LENGTH: 28
<212> TYPE: DNA
<213> ORGANISM: Artificial Sequence
<220> FEATURE:
<223> OTHER INFORMATION: Primer 2 for FGA

<400> SEQUENCE: 46
actcacagat taaactgtaa ccaaaata                              28

<210> SEQ ID NO 47
<211> LENGTH: 26
<212> TYPE: DNA
<213> ORGANISM: Artificial Sequence
<220> FEATURE:
<223> OTHER INFORMATION: Primer 1 for CSF 1PO

<400> SEQUENCE: 47
ctgccttcat agatagaaga tagata                                26

<210> SEQ ID NO 48
<211> LENGTH: 24
<212> TYPE: DNA
<213> ORGANISM: Artificial Sequence
<220> FEATURE:
<223> OTHER INFORMATION: Primer 2 for CSF 1PO

<400> SEQUENCE: 48
ctcagaccct gttctaagta cttc                                  24

<210> SEQ ID NO 49
<211> LENGTH: 27
<212> TYPE: DNA
<213> ORGANISM: Artificial Sequence
<220> FEATURE:
<223> OTHER INFORMATION: Primer 1 for vWA

<400> SEQUENCE: 49
gtggatgata agaataatca gtatgtg                               27

<210> SEQ ID NO 50
```

```
<211> LENGTH: 30
<212> TYPE: DNA
<213> ORGANISM: Artificial Sequence
<220> FEATURE:
<223> OTHER INFORMATION: Primer 2 for vWA

<400> SEQUENCE: 50
attttggaca gatgataaat acataggatg                                30

<210> SEQ ID NO 51
<211> LENGTH: 27
<212> TYPE: DNA
<213> ORGANISM: Artificial Sequence
<220> FEATURE:
<223> OTHER INFORMATION: Primer 1 for D1S1656

<400> SEQUENCE: 51
gattctcctt cagtcctgtg ttagtca                                   27

<210> SEQ ID NO 52
<211> LENGTH: 23
<212> TYPE: DNA
<213> ORGANISM: Artificial Sequence
<220> FEATURE:
<223> OTHER INFORMATION: Primer 2 for D1S1656

<400> SEQUENCE: 52
ggtggtagag atggaagaaa atc                                       23

<210> SEQ ID NO 53
<211> LENGTH: 29
<212> TYPE: DNA
<213> ORGANISM: Artificial Sequence
<220> FEATURE:
<223> OTHER INFORMATION: Primer 1 for Penta E

<400> SEQUENCE: 53
gatgtgtgta aagtgcttag tatcatgat                                 29

<210> SEQ ID NO 54
<211> LENGTH: 25
<212> TYPE: DNA
<213> ORGANISM: Artificial Sequence
<220> FEATURE:
<223> OTHER INFORMATION: Primer 2 for Penta E

<400> SEQUENCE: 54
tgaaaaatta gctgggtgtg gtggt                                     25
```